US009834515B2

(12) United States Patent
Bhattacharya et al.

(10) Patent No.: US 9,834,515 B2
(45) Date of Patent: Dec. 5, 2017

(54) PROCESS FOR SYNTHESIS OF PIPERIDINE ALKALOIDS (71) Applicant: Council of Scientific and Industrial Research, New Delhi (IN)

(72) Inventors: Asish Kumar Bhattacharya, Pune (IN); Hemender Rami Chand, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 15/309,873

(22) PCT Filed: May 5, 2015

(86) PCT No.: PCT/IN2015/000196
§ 371 (c)(1),
(2) Date: Nov. 9, 2016

(87) PCT Pub. No.: WO2015/170339
PCT Pub. Date: Nov. 12, 2015

(65) Prior Publication Data
US 2017/0267636 A1 Sep. 21, 2017

(30) Foreign Application Priority Data
May 9, 2014 (IN) .......................... 1250/DEL/2014

(51) Int. Cl.
*C07D 211/46* (2006.01)
*C07D 211/74* (2006.01)
*C07H 5/04* (2006.01)

(52) U.S. Cl.
CPC .......... *C07D 211/74* (2013.01); *C07D 211/46* (2013.01); *C07H 5/04* (2013.01)

(58) Field of Classification Search
CPC ........ C07D 211/46; C07D 211/74; C07H 5/04
See application file for complete search history.

(56) References Cited

U.S. PATENT DOCUMENTS 8,445,670 B2 * 5/2013 Moriarty .............. C07D 207/12
536/55.3

FOREIGN PATENT DOCUMENTS

WO WO-2015/170339 11/2015

OTHER PUBLICATIONS

"International Application No. PCT/IN2015/000196, International Search Report and Written Opinion dated Aug. 14, 2015", (Aug. 14, 2015), 10 pgs.
Bates, Roderick W., "A synthesis of 2-epi-fagomine using gold(I)-catalysed allene cyclisation", Tetrahedron Letters, vol. 52, Issue 23, Jun. 8, 2011, pp. 2969-2971, (Jun. 8, 2011), 2969-2971.
Desire, Jerome, et al., "Chemistry of Imino Glycals: Preparation and Application to the Synthesis of (+)-Fagomine", Synlett 2001; 2001(8): 1329-1331, (2001), 1329-1331.
Diez, J. Alberto, et al., "Stereoselective synthesis and biological evaluation of D-fagomine, D-3-epi-fagomine and D-3,4-epi-fagomine analogs from D-glyceraldehyde acetonide as a common building block", Org. Biomol. Chem., 2012,10, 9278-9286, (Oct. 11, 2012), 9278-9286.
Goujon, Jean-Yves, et al., "General synthesis and biological evaluation of a-1-C-substituted derivatives of fagomine (2-deoxynojirimycin-a-C-glycosides)", Bioorganic & Medicinal Chemistry, vol. 13, Issue 6, Mar. 15, 2005, pp. 2313-2324, (Mar. 15, 2005), 2313-2324.
Guo, Lian-Dong, et al., "A Concise and Divergent Approach to Hydroxylated Piperidine Alkaloids and Azasugar Lactams", European Journal of Organic Chemistry, vol. 2013, Issue 11, Apr. 2013, 2230-2236, (Apr. 2013), 2230-2236.
Kumar, K.S. Ajish, et al., "Divergent Synthesis of 4-epi-Fagomine, 3,4-Dihydroxypipecolic Acid, and a Dihydroxyindolizidine and Their β-Galactosidase Inhibitory and Immunomodulatory Activities", J. Org. Chem., 2013, 78 (15), pp. 7406-7413, (Jun. 27, 2013), 7406-7413.
Kumari, Nitee, et al., "Efficient and Stereodivergent Syntheses of D- and L-Fagomines and Their Analogues", European Journal of Organic Chemistry, vol. 2009, Issue 1, Jan. 2009, 160-169, (Nov. 25, 2008), 160-169.
Okaki, Toru, et al., "Stereoselective Total Synthesis of (−)-Batzellasides A, B, and C", European Journal of Organic Chemistry, vol. 2013, Issue 14, May 2013, 2841-2848, (May 2013), 2841-2848.
Squarcia, Antonella, et al., "Glycal-mediated syntheses of enantiomerically pure polyhydroxylated ?- and d-lactams", Tetrahedron Letters, vol. 43, Issue 26, May 28, 2002, pp. 4653-4655, (May 28, 2002), 4653-4655.

* cited by examiner

*Primary Examiner* — Timothy R Rozof
(74) *Attorney, Agent, or Firm* — Schwegman Lundberg & Woessner, P.A.

(57) ABSTRACT

The present invention discloses a process for synthesis of piperidine alkaloids selected from fagomine, 4-epi-fagomine and nojirimycin from tri-O-benzyl-D-glucal or tri-O-benzyl-D-galactal.

6 Claims, 2 Drawing Sheets

PROCESS FOR SYNTHESIS OF PIPERIDINE ALKALOIDS

PRIORITY CLAIM TO RELATED APPLICATIONS

This application is a U.S. national stage application filed under 35 U.S.C. §371 from International Application Serial No. PCT/IN2015/000196, which was filed 5 May 2015, and published as WO2015/170339 on 12 Nov. 2015, and which claims priority to Indian Application No. 1250/DEL/2014, filed 9 May 2014, which applications and publication are incorporated by reference as if reproduced herein and made a part hereof in their entirety, and the benefit of priority of each of which is claimed herein.

FIELD OF THE INVENTION

The present invention relates to a process for synthesis of piperidine alkaloids. Particularly, present invention relates to a process for synthesis of piperidine alkaloids selected from fagomine, 4-epi-fagomine and nojirimycin.

BACKGROUND AND PRIOR ART OF THE INVENTION

Polyhydroxylated piperidines and their synthetic analogues have attracted a great deal of attention in recent years due to their ability to mimic sugars, and competitively and selectively inhibit glycosidases and glycosyltransferases, the carbohydrate processing enzymes. These attributes make hydroxylated piperidines (azasugars) likely therapeutic agents for the treatment of diseases related to metabolic disorders involving carbohydrates such as diabetes, cancer, AIDS, and viral infections, where glycoprotein processing is crucial. Recently three fagomine and some of its isomers were found from *Xanthocercis zambesiaca* occurring in southern Africa in dry forest. Among them, fagomine and 3-epi-fagomine have been shown to have activity against mammalian α-glucosidase and β-galactosidase. More recently fagomine was found to have a potent antihyperglycaemic effect in streptozocin-induced diabetic mice and a potentiation of glucose-induced insulin secretion.

Figure 1:
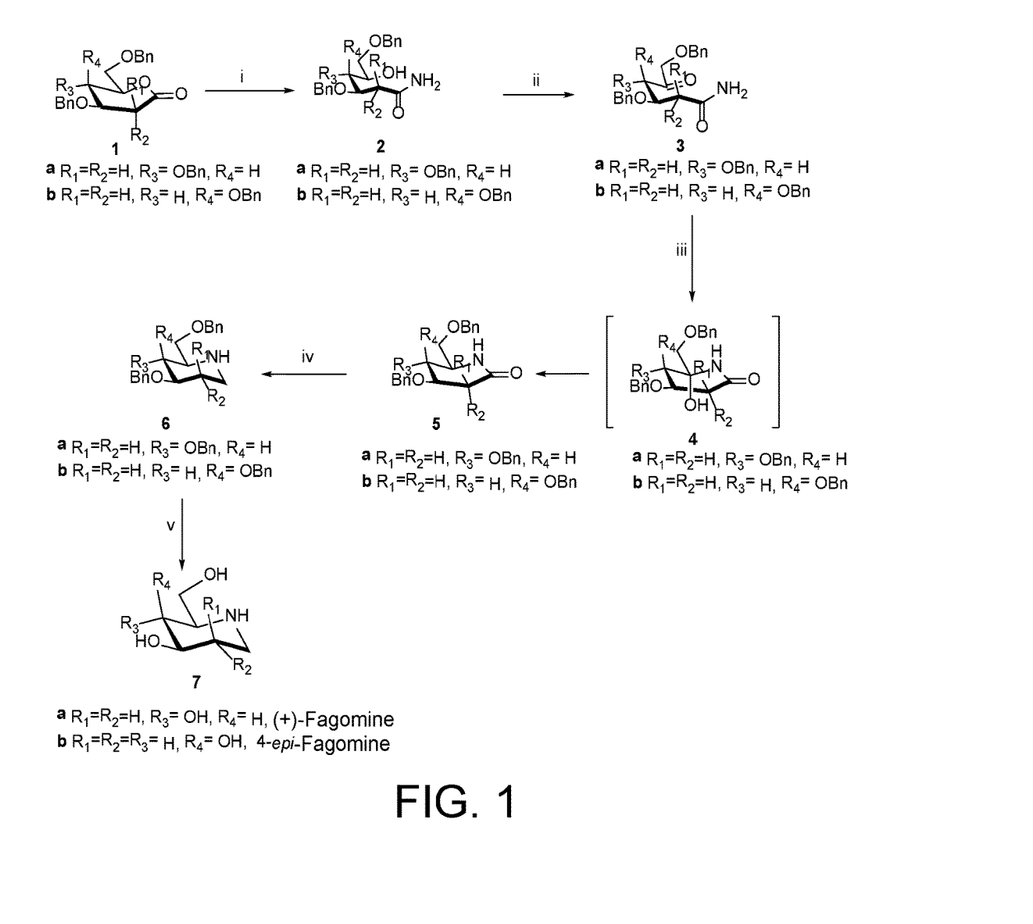
FIG. 1 deipcts Scheme 1, which represents processes for the synthesis of (+)-fagomine and 4-epi-fagomine.
Figure 2:
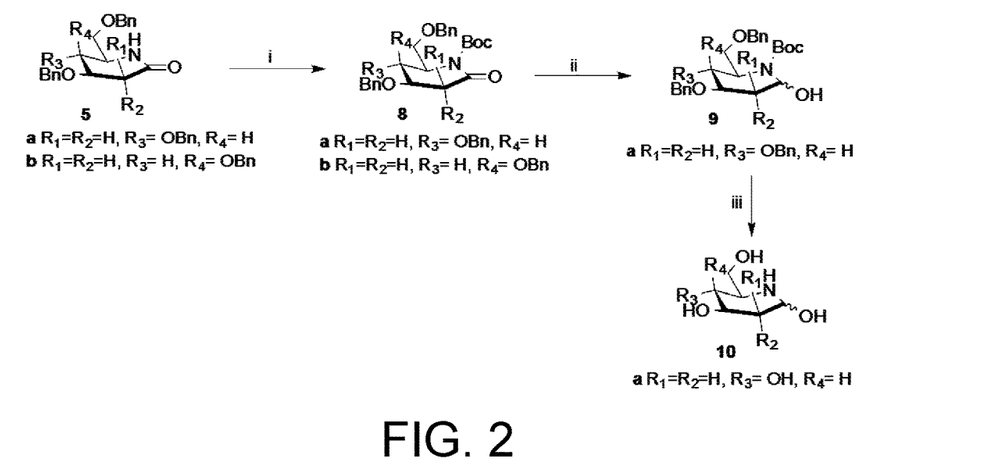
FIG. 2 depicts Scheme 2, which represents process for the synthesis of 3-deoxynojirimycin.
Figure 3:
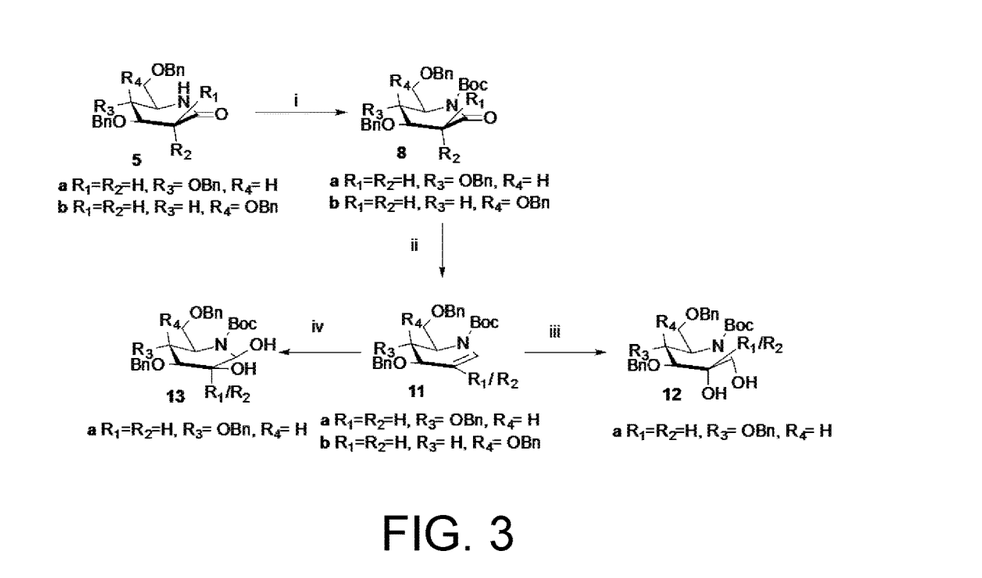
FIG. 3 depicts Scheme 3, which represents process for the synthesis of piperidine alkaloids (imino glycals).

FIG 1. Some glycosidase or galactosidase inhibitors belonging to piperidine class of alkaloid.

Nojirimycin
Adenophorine
5-Deoxyadenophorine
β-1-C-butyl-deoxy-galactonojirimycin (2S)-Carboxy-(3R,4R,5S)-trihydroxypiperidine
Fagomine
4-epi-Fagomine
2-deoxyNojirimycin Glycals, carbohydrates incorporating a double bond between C-1 and C-2, have emerged as powerful building blocks in synthetic chemistry especially in the context of oligosaccharide assembly. In light of this fact, it is perhaps surprising that the synthesis and chemistry of imino glycals, glycals in which the ring oxygen atom is replaced by nitrogen, has not been explored in a systematic fashion. Such compounds should participate in a diverse range of reactions (e.g. addition and cycloadditions reactions, metal catalyzed cross-couplings), and thus provide access to many potentially useful classes of imino sugars which are of interest because of their ability to influence a variety of biological processes by the inhibition of the glycosidase enzymes. Furthermore, imino glycals might serve as precursors to various glycosyl donors which could be used to make oligosaccharides incorporating nitrogen atoms, another area of current interest.

Article titled "Stereoselective synthesis and biological evaluation of D-fagomine, D-3-epi-fagomine and D-3,4-epi-fagomine analogs from D-glyceraldehyde acetonide as a common building block" by JA Díez et al. Published in *Org Biomol Chem.*, 2012; 10(46), pp 9278-86 reports synthesis involves diastereoselective anti-vinylation of its homoallylimine, ring-closing metathesis, and stereoselective epoxidation followed by regioselective ring-opening or stereoselective dihydroxylation.

Article titled "Efficient and stereodivergent syntheses of D- and L-fagomines and their analogues" by N Kumari et al. published in *European Journal of Organic Chemistry*, 2009, 2009 (1), pp 160-169 reports the synthesis of d- and 1-fagomines 1, 4, 5 and 6 and their isomers from starting d-glycals. The syntheses involve elaboration of common amino alcohol precursors obtained from 2-deoxy-1-amino sugar derivatives. The key steps in the synthesis are intramolecular reductive amination and intramolecular N-heterocyclization.

Article titled "A divergent synthesis of 4-epi-fagomine, 3, 4-dihydroxypipecolic acid, and a dihydroxyindolizidine and their beta-galactosidase inhibitory and immunomodulatory activities" by KS Kumar et al. published in *J Org Chem.*, 2013, 78(15), pp 7406-13 reports a divergent asymmetric synthesis of the iminosugars starting from a chiral homoallyl alcohol as the versatile intermediate. The homoallyl alcohol is prepared by a highly diastereoselective Barbier reaction on a D-glucose-derived aldehyde. The protection of hydroxyl function followed by reductive ozonolysis of the olefin and a subsequent one-pot three-step protocol involving a Staudinger reaction, reductive amination, and benzyloxy carbonyl protection yielded an important bicyclic furanopiperidine derivative.

Article titled "A synthesis of 2-epi-fagomine using gold (I)-catalyzed allene cyclisation" by Bates et al. published in a synthesis of 2-epi-fagomine via a highly stereoselective gold(I)-catalyzed allene cyclisation. A highly stereoselective Au(I)-catalyzed cyclization of allene (IV) is the key step in the synthesis of 2-epi-fagomine (VI).

Article titled "General synthesis and biological evaluation of alpha-1-C-substituted derivatives of fagomine (2-deoxynojirimycin-alpha-C-glycosides)" by JY Goujon et al. published in *Bioorg Med Chem.*, 2005, 13(6), pp 2313-24 reports a general synthesis of alpha-1-C-substituted derivatives of fagomine (2-deoxynojirimycin-alpha-C-glycosides) by ring-opening reactions of an aziridine with various heteroatomic nucleophiles, including thiol, amine, alcohol, carboxylate and phosphate. This nine-step reaction sequence proceeded in an overall yield of 14-28% from tri-O-benzyl-D-glucal.

Article titled "Chemistry of imino glycals: preparation and application to the synthesis of (+)-fagomine" by J Desire et al. published in *Synlett,* 2001, 2001 (8), 1329-1331 reports the synthesis of imino glucal from tri-O-benzyl-D-glucal in 8 steps. This novel imino sugar building block is further converted into (+)-fagomine by a two-step hydrogenation sequence.

The prior art processes had many drawbacks such as poor yield and longer reaction sequence. Therefore there is need in the art to develop a shorter process for the preparation of piperidine alkaloids selected from (+)-fagomine, 4-epi-fagomine and nojirimycin with better yield.

OBJECTIVE OF INVENTION

The main objective of the present invention is to provide a process for the synthesis of piperidine alkaloids from glucal or galactal.

Another objective of the present invention is to provide a process for the synthesis of (+)-fagomine, 4-epi-fagomine and 3-deoxynojirimycin from glucal or galactal.

SUMMARY OF THE INVENTION

Accordingly, present invention provides a process for the preparation of piperidine alkaloids comprising the steps of:
a) dissolving gluconolactone compound (1) in methanolic ammonia solution followed by stirring at room temperature in the range of 20 to 35° C. for 1 to 1.5 h to afford 5-δ-hydroxy amide (2);

1a $R_1=R_2=H$, $R_3=OBn$, $R_4=H$
1b $R_1=R_2=H$, $R_3=H$, $R_4=OBn$

2a $R_1=R_2=H$, $R_3=OBn$, $R_4=H$
2b $R_1=R_2=H$, $R_3=H$, $R_4=OBn$ b) stirring a solution of compound 2 as obtained in step (a) in DMSO and $Ac_2O$ at room temperature in the range of 20 to 35° C. for period in the range of 22 to 23 h followed by addition of water to afford δ-keto amide (3);

3a $R_1 = R_2 = H$, $R_3 = OBn$, $R_4 = H$
3b $R_1 = R_2 = H$, $R_3 = H$, $R_4 = OBn$ c) adding formic acid and sodium cyanoborohydride to a solution of compound 3 as obtained in step (b) in acetonitrile followed by refluxing at temperature in the range of 80 to 85° C. for period in the range of 4 to 4.5 h to afford glycolactam compound (5);

5a $R_1 = R_2 = H$, $R_3 = OBn$, $R_4 = H$
5b $R_1 = R_2 = H$, $R_3 = H$, $R_4 = OBn$ d) adding lithium aluminium hydride to a solution of compound 5 as obtained in step (c) in tetrahydrofuran followed by stirring the reaction mixture for period in the range of 3.5 to 4 h at temperature in the range of 65 to 70° C. and purification to afford protected piperidine compound (6);

6a $R_1 = R_2 = H$, $R_3 = OBn$, $R_4 = H$
6b $R_1 = R_2 = H$, $R_3 = H$, $R_4 = OBn$ e) adding palladium on active charcoal to a solution of piperidine compound 6 as obtained in step (d) in acetic acid followed by stirring the mixture for overnight for period in the range of 10 to 12 hr at room temperature in the range of 20 to 35° C. under hydrogen atmosphere to afford piperidine alkaloids (7);

7a $R_1 = R_2 = H, R_3 = OH, R_4 = H$, (+)-Fagomine
7b $R_1 = R_2 = R_3 = H, R_4 = OH$, 4-epi-Fagomine f) adding $Et_3N$ to a solution of glycolactam (5) as obtained in step (c) in dichloromethane followed by cooling to 0° C. and further adding $Boc_2O$, DMAP followed by stirring at temperature in the range of 20 to 25° C. for period in the range of 8 to 9 h to afford N-Boc protected lactam (8);

8a $R_1 = R_2 = H, R_3 = OBn, R_4 = H$
8b $R_1 = R_2 = H, R_3 = H, R_4 = OBn$ g) dissolving N-Boc protected lactam (8a) of step (d) in toluene and cooling to −76° C. under inert atmosphere and adding superhydride and ammonium chloride solution at −76° C. followed by stirring the reaction mixture for period in the range of 9 to 10 h at room temperature to afford lactamol compound 9a;

9a $R_1 = R_2 = H, R_3 = OBn, R_4 = H$ h) stirring a mixture of compound of step (e) and HCl in methanol at 70° C. for 5 h followed by basifying the reaction mixture to afford 3-deoxynojirimycin (10a).

10a $R_1 = R_2 = H, R_3 = OH, R_4 = H$ i) dissolving N-Boc protected lactam (8a) of step (d) in dry toluene and cooled at −76° C. under inert atmosphere and adding superhydride with stirring followed by addition of TFAA, DIPEA, catalytic amount of DMAP and purification to afford Boc-iminoglycal (11a/11b);

j) adding Boc-iminoglycal (11a) to a solution of $(DHQ)_2$AQN, $K_3Fe(CN)_6$, $K_2CO_3$, $K_2OsO_2(OH)_4$ and $CH_3SO_2NH_2$ in tert-butyl alcohol and water cooled at 0° C. followed by stirring the mixture at 0° C. for 60 to 66 h to afford iminoglycal compound (12a);

k) The process as claimed in any of the preceding claims, wherein said process may also comprises adding Boc-iminoglycal (11a) to a solution of $(DHQD)_2AQN$, $K_3Fe(CN)_6$, $K_2CO_3$, $K_2OsO_2(OH)_4$ and $CH_3SO_2NH_2$ in tert-butyl alcohol and water cooled at 0° C. followed by stirring the mixture at 0° C. for 60 to 66 h to afford iminoglycal compound (13a).

In an embodiment of the present invention, the piperidine alkaloids are (+)-fagomine (7a), 4-epi-fagomine (7b), 3-deoxynojirimycin (10a).

In another embodiment of the present invention, the steps (a), (b) and (d) are carried out under nitrogen atmosphere.

In yet another embodiment of the present invention, the process may also comprises dissolving N-Boc protected lactam (8a) of step (d) in dry toluene and cooled at −76° C. under inert atmosphere and adding superhydride with stirring followed by addition of TFAA, DIPEA, catalytic amount of DMAP and purification to afford Boc-iminoglycal (11a/11b).

In yet another embodiment of the present invention, the Boc-iminoglycal is tert-butyl (2R,3R)-3,4-bis(benzyloxy)-2-((benzyloxy)methyl)-3,4-dihydropyridine-1(2H)-carboxylate (11a), tert-butyl (2R,3S)-3,4-bis(benzyloxy)-2-((benzyloxy)methyl)-3,4-dihydropyridine-1(2H)-carboxylate (11b).

In yet another embodiment of the present invention, said process may also comprise adding Boc-iminoglycal (11a/11b) to a solution of $(DHQ)_2AQN$, $K_3Fe(CN)_6$, $K_2CO_3$, $K_2OsO_2(OH)_4$ and $CH_3SO_2NH_2$ in tert-butyl alcohol and water cooled at 0° C. followed by stirring the mixture at 0° C. for 60 to 66 h to afford iminoglycal compound (12).

In yet another embodiment of the present invention, said process may also comprises adding Boc-iminoglycal (11a) to a solution of $(DHQD)_2AQN$, $K_3Fe(CN)_6$, $K_2CO_3$, $K_2OsO_2(OH)_4$ and $CH_3SO_2NH_2$ in tert-butyl alcohol and water cooled at 0° C. followed by stirring the mixture at 0° C. for 60 to 66 h to afford iminoglycal compound (13a).

In yet another embodiment of the present invention, the iminoglycal compound is tert-Butyl (2R,3R,5R,6R)-3,4-bis(benzyloxy)-2-((benzyloxy)methyl)-5,6-dihydroxy-piperidine-1-carboxylate (12a) or tert-Butyl (2R,3R,5S,6S)-3,4-bis(benzyloxy)-2-((benzyloxy)methyl)-5,6-dihydroxypiperidine-1-carboxylate (13a).

DETAILED DESCRIPTION OF THE INVENTION

Present invention provides a process for the synthesis of piperidine alkaloids starting from glucal or galactal.

In an aspect, the present invention provides a process for the synthesis of (+)-fagomine and 4-epi-fagomine starting from glucal or galactal.

In another aspect, the present invention provides a process for the synthesis of 3-deoxynojirimycin starting from glucal or galactal.

The present invention provides a process for the synthesis of piperidine alkaloids selected from (+)-fagomine and 4-epi-fagomine in 14% and 6% overall yields and the said process comprising the steps of:
  a) dissolving gluconolactone compound (1a/1b) in methanolic ammonia solution followed by stirring at room temperature in the range of 20 to 35° C. for 6 h under nitrogen atmosphere to afford δ-hydroxy amide (2a/2b);
  b) stirring a solution of compound of step (a) in DMSO and $Ac_2O$ at room temperature in the range of 20 to 35° C. for 23 h under nitrogen atmosphere followed by addition of water to obtain a yellow oil precipitate of 5-keto amide (3a/3b);
  c) adding formic acid and sodium cyanoborohydride to a solution of compound of step (b) in acetonitrile followed by refluxing the reaction mixture at 85° C. for 4.5 h to afford glycolactam compound (5a/5b);
  d) adding lithium aluminium hydride to a solution of compound of step (c) in tetrahydrofuran followed by stirring the reaction mixture for 4 h at 70° C. under nitrogen atmosphere and purification to afford protected piperidine compound (6a/6b) as a yellow syrup;
  e) adding 10% palladium on active charcoal to a solution of compound of step (d) in acetic acid followed by stirring the mixture for overnight at room temperature under hydrogen atmosphere to afford piperidine alkaloids selected from (+)-fagomine (7a) and 4-epi-fagomine (7b).

The compounds formed in step (a) are (3R,4R)-3,4,6-Tris(benzyloxy)-5-hydroxyhexanamide (2a) and (3R,4S)-3,4,6-tris(benzyloxy)-5-hydroxyhexanamide (2b).

The compounds formed in step (b) are (3R,4S)-3,4,6-Tris(benzyloxy)-5-oxohexanamide (3a) and (3R,4R)-3,4,6-Tris(benzyloxy)-5-oxohexanamide (3b).

The glycolactam compounds formed in step (c) are (5R,6R)-4,5-Bis(benzyloxy)-6-(benzyloxymethyl)piperidin-2-one (5a), (5S,6R)-4,5-Bis(benzyloxy)-6-(benzyloxymethyl)piperidin-2-one (5b).

The compounds formed in step (d) are (2R,3R,4R)-3,4-Bis(benzyloxy)-2-(benzyloxymethyl)piperidine (6a), (2R,3S,4R)-3,4-Bis(benzyloxy)-2-(benzyloxymethyl) piperidine (6b).

The present invention provides a process for the synthesis of 3-deoxynojirimycin (10a) starting from glucal or galactal and the said process comprising the steps of:
  a) dissolving gluconolactone compound (1a/1b) in methanolic ammonia solution followed by stirring at room temperature in the range of 20 to 35° C. for 1.5 h under nitrogen atmosphere to afford δ-hydroxy amide (2a/2b);
  b) stirring a solution of compound of step (a) in DMSO and $Ac_2O$ at room temperature in the range of 20 to 35° C. for 23 h under nitrogen atmosphere followed by addition of water to obtain a yellow oil precipitate of δ-keto amide (3a/3b);
  c) adding formic acid and sodium cyanoborohydride to a solution of compound of step (b) in acetonitrile followed by refluxing the reaction mixture at 85° C. for 4.5 h to afford glycolactam compound (5a/5b);
  d) adding Et3N to a solution of glycolactam (5a/5b) of step (c) in dichloromethane followed by cooling to 0° C. and further adding Boc2O, DMAP followed by stirring at 25° C. for 9 h to afford N-Boc protected lactam (8a/8b);
  e) dissolving N-Boc protected lactam (8a/8b) of step (d) in toluene and cooling to −76° C. under inert atmosphere and adding superhydride and ammonium chloride solution at −76° C. followed by stirring the reaction mixture for 10 h at room temperature to afford lactamol (9a);
  f) stirring a mixture of compound of step (e) and HCL in methanol at 70° C. for 5 h followed by basifying the reaction mixture to afford 3-deoxyNojirimycin (10).

The N-Boc protected lactam compound formed in step (d) are Tert-butyl (2R,3R,4S)-3,4-bis(benzyloxy)-2-((benzyloxy)methyl)-6-oxopiperidine-1-carboxylate (8a), Tert-butyl (2R,3S,4S)-3,4-Bis(benzyloxy)-2-((benzyloxy)methyl)-6-oxopiperidine-1-carboxylate (8b).

The carboxylate compound formed in step (e) is tert-butyl (2R,3R)-3,4-bis(benzyloxy)-2-((benzyloxy)methyl)-6-hydroxypiperidine-1-carboxylate (9a).

The present invention provides a process for the synthesis of piperidine alkaloids (imino glycals) comprising the steps of:
  a) dissolving gluconolactone compound (1a/1b) in methanolic ammonia solution followed by stirring at room temperature for 1.5 h under nitrogen atmosphere to afford δ-hydroxy amide (2a/2b);
  b) stirring a solution of compound of step (a) in DMSO and $Ac_2O$ at room temperature for 23 h under nitrogen atmosphere followed by addition of water to obtain a yellow oil precipitate of δ-keto amide (3a/3b);
  c) adding formic acid and sodium cyanoborohydride to a solution of compound of step (b) in acetonitrile followed by refluxing the reaction mixture for 4.5 h to afford glycolactam compound (5a/5b);
  d) adding $Et_3N$ to a solution of glycolactam (5a/5b) of step (c) in dichloromethane followed by cooling to 0° C. and further adding $Boc_2O$, DMAP followed by stirring at 25° C. for 9 h to afford N-Boc protected lactam (8a/8b);
  e) dissolving N-Boc protected lactam (8a/8b) of step (d) in dry toluene and cooling under inert atmosphere, and adding superhydride with stirring followed by addition of TFAA, DIPEA, catalytic amount of DMAP and purification to afford Boc-iminoglycal (11a/11b).
  f) adding Boc-iminoglycal (11a) to a solution of $(DHQ)_2$ AQN, $K_3Fe(CN)_6$, $K_2CO_3$, $K_2OsO_2(OH)_4$ and $CH_3SO_2NH_2$ in tert-butyl alcohol and water cooled at 0° C. followed by stirring the mixture at 0° C. for 60 to 66 h to afford iminoglycal compound (12a).
  g) adding Boc-iminoglycal (11a) to a solution of $(DHQD)_2$ AQN, $K_3Fe(CN)_6$, $K_2CO_3$, $K_2OsO_2(OH)_4$ and $CH_3SO_2NH_2$ in tert-butyl alcohol and water cooled at 0° C. followed by stirring the mixture at 0° C. for 60 to 66 h to afford iminoglycal compound (13a).

The Boc-iminoglycal formed in step (e) is tert-butyl (2R,3R)-3,4-bis(benzyloxy)-2-((benzyloxy)methyl)-3,4-dihydropyridine-1(2H)-carboxylate (11a), Tert-butyl (2R,3S)-3,4-bis(benzyloxy)-2-((benzyloxy)methyl)-3,4-dihydropyridine-1(2H)-carboxylate (11b).

The iminoglycal compound is tert-Butyl (2R,3R,5R,6R)-3,4-bis(benzyloxy)-2-((benzyloxy)methyl)-5,6-dihydroxypiperidine-1-carboxylate (12a) or tert-Butyl (2R,3R,5S,6S)-3,4-bis(benzyloxy)-2-((benzyloxy)methyl)-5,6-dihydroxypiperidine-1-carboxylate (13a).

EXAMPLES

Following examples are given by way of illustration and therefore should not be construed to limit the scope of the invention.

Example 1

Preparation of (+)-fagomine and 4-epi-fagomine

Example 1 (A)

Preparation of (3R,4R)-3,4,6-Tris(benzyloxy)-5-hydroxyhexanamide (2a)

Gluconolactone 1a (1.393 g, 2.32 mmol) was dissolved in methanolic ammonia soln. (7N, 22 mL) and was stirred at room temperature 25° C. for 6 h. After completion of the reaction (TLC), reaction mixture was concentrated in vacuo followed by purification by $SiO_2$ column chromatography (EtOAc-petroleum ether, 6:4) to afford 2a (859 mg, 82%) as colorless solid; mp 74-76° C.

$R_f$ 0.26 (EtOAc-petroleum ether, 1:1); $[\alpha]^{20}_D$+14.27 (c 1.43, $CHCl_3$); IR ($CHCl_3$): $\nu_{max}$ 3374, 3201, 3012, 2869, 1673, 1615, 1404, 1216, 1072, 1028, 908, 747, 698, 667 $cm^{-1}$; $^1$H NMR (200 MHz, $CDCl_3$, assignment by COSY, HSQC and HMBC experiments): $\delta_H$ 7.33-7.24 (m, 15H, ArH), 5.76 (bs, 1H, NH), 5.45 (bd, 1H, NH), 4.61-4.47 (m, 6H, Ph-$CH_2$), 4.31-4.23 (m, 1H, H-3), 3.99-3.92 (m, 1H, H-5), 3.67-3.62 (m, 3H, H-4, H-6), 3.14 (bs, 1H, OH), 2.52-2.57 (m, 2H, H-2); $\delta_C$ (100 MHz, $CDCl_3$) 173.5 (q, C-1) 138.0, 137.8, 137.6 (q, Ar), 128.5, 128.4, 128.3, 128.0, 127.8 (s, Ar), 78.2 (s, C-4), 76.6 (s, C-3), 73.5 (d, —$OCH_2Ph$), 73.4 (d, 2C, C-6, —$OCH_2Ph$), 71.2 (d, —$OCH_2Ph$), 70.8 (s, C-5), 37.3 (d, C-2); ESI-MS: m/z 450.2240 (M+H)$^+$; HRMS: m/z calcd for $C_{27}H_{31}NO_5$ 449.22022, found 449.20571.

Example 1 (B)

Preparation of (3R,4S)-3,4,6-tris(benzyloxy)-5-hydroxyhexanamide (2b)

Galactonolactone 1b (2.0 g, 4.65 mmol) was dissolved in methanolic ammonia soln. (7N, 25 mL) and stirred at room temperature 27° C. for 11 h under nitrogen atmosphere. After completion of the reaction (TLC), reaction mixture was concentrated in vacuo to furnish a crude which was purified by $SiO_2$ column chromatography (EtOAc-petroleum ether, 1:1) to afford 2b (1.997 g, 96%) as yellowish gum.

$R_f$ 0.19 (EtOAc-petroleum ether, 1:1); $[\alpha]^{20}_D$+2.92 (c 1.2, $CHCl_3$); IR ($CHCl_3$): $\nu_{max}$ 3660, 3372, 3019, 2872, 1736, 1454, 1216, 1101, 1064, 908, 755, 698, 668 $cm^{-1}$; $^1$H NMR (200 MHz, $CDCl_3$, assignment by COSY, HSQC and HMBC experiments, $D_2O$ exchange): $\delta_H$ 7.33-7.25 (m, 15H, ArH), 6.00 (bs, 1H, NH), 5.51 (bs, 1H, NH), 4.79-4.48 (m, 6H, $PhCH_2$), 4.18-4.10 (m, 1H, H-3), 3.95 (bs, 1H, H-4), 3.76-3.72 (m, 1H, H-5), 3.60-3.44 (m, 2H, H-6), 2.83 (bs, 1H, OH), 2.68-2.47 (m, 2H, H-2); $^{13}$C NMR (50 MHz, $CDCl_3$): $\delta_C$ 173.6 (q, C-1), 137.8, 137.7 (q, Ar), 128.6, 128.5, 128.1, 128.0, 127.9 (s, Ar), 78.8 (s, C-4), 77.3 (s, C-3), 74.1, 73.5, 73.0, 71.1 (d, $PhCH_2$, C-6), 69.9 (s, C-5), 37.7 (d, C-2); ESI-MS: m/z 450.4348 (M+H)$^+$, 472.4115 (M+Na)$^+$, 487.5341 (M+K)$^+$; HRMS: m/z calcd for $C_{27}H_{31}NO_5$ 449.22022, found 449.20571.

Example 1 (C)

Preparation of (3R,4S)-3,4,6-Tris(benzyloxy)-5-oxohexanamide (3a)

A solution of 2a (1.105 g, 2.5 mmol) in DMSO (11 mL) and $Ac_2O$ (6.7 mL) was stirred under nitrogen atmosphere for 23 h. Water (50 mL) was added and the mixture was stirred for another 15 minutes during which a yellow oil precipitated. The water layer was then removed and the residue was washed with water (3×50 mL). The residue was dissolved in DCM (25 mL) and extracted with brine (2×50 mL). The organic layers were dried (anhyd. $Na_2SO_4$) and concentrated in vacuo to afford crude 3a (59%). The crude obtained was used as such for the next step.

Example 1 (D)

Preparation of (3R,4R)-3,4,6-Tris(benzyloxy)-5-oxohexanamide (3b)

A solution of 2b (1.105 g, 2.5 mmol) in DMSO (11 mL) and $Ac_2O$ (6.7 mL) was stirred under nitrogen atmosphere for 26 hours at room temperature 22° C. $H_2O$ (50 mL) was added and the reaction mixture was stirred for another 15 minutes during which a yellow oil precipitated. The water layer was then removed and the residue was washed with water (3×50 mL). The residue was dissolved in DCM (25 mL) and extracted with brine (2×50 mL). The organic fractions were dried (anhyd. $Na_2SO_4$) and concentrated in vacuo to afford crude 3b (24%). The crude obtained was used as such for the next step.

Example 1 (E)

Preparation of (5R,6R)-4,5-Bis(benzyloxy)-6-(benzyloxymethyl)piperidin-2-one (5a)

Compound 3a (582 mg, 1.302 mmol) was dissolved in MeCN (20 mL) and HCOOH (3.8 mL) was added to the reaction mixture followed by $NaCNBH_3$ (177 mg, 2 eqs.) and the reaction mixture was refluxed at 85° C. for 4.5 h. The reaction mixture was then cooled in an ice-bath and was quenched by adding aq. HCl solution (0.1 N, 30 mL). After stirring for another 15 minutes, EtOAc (50 mL) and then saturated aq. $NaHCO_3$ solutions (50 mL) were added to it. The water layer was separated and extracted with EtOAc (2×25 mL), the combined organic fractions were pooled and then washed with brine (1×30 mL) and dried (anhyd. $Na_2SO_4$). After concentration in vacuo, the resulting crude was purified by $SiO_2$ column chromatography (EtOAc-petroleum ether, 4:6) to afford a white solid which on crystallization (EtOAc-petroleum ether) furnished 5a as colorless needles. (329 mg, 59%); mp 73-75° C.; $R_f$ 0.32 (EtOAc-petroleum ether, 1:1); $[\alpha]^{20}_D$+16.78 (c1.02, $CHCl_3$); IR ($CHCl_3$): $\nu_{max}$ 3396, 3019, 2868, 1666, 1455, 1215, 1100, 755, 699, 669 $cm^{-1}$; $^1$H NMR (200 MHz, CDCl$_3$): δ$_H$ 7.39-7.21 (m, 15H, ArH), 6.16 (bs, 1H, NH), 4.84-4.46 (m, 6H, PhCH$_2$), 3.94-3.84 (m, 1H, H-6), 3.69-3.49 (m, 3H, H-6, H-3, H-4), 3.41-3.32 (m, 1H, H-5), 2.86-2.42 (m, 2H, H-2); $^{13}$C NMR (50 MHz, CDCl$_3$): δ$_C$ 169.6 (q, C-1, C=O), 137.7, 137.6, 137.4 (q, Ar), 128.5, 128.1, 127.9, 127.7, 127.6 (s, CH, Ar), 75.8 (s, C-4), 75.6 (s, C-3), 73.7, 73.4, 71.7 (d, —CH$_2$Ph), 71.0 (d, C-6), 54.8 (s, C-5), 35.2 (d, C-2); ESI-MS: m/z 432.7864 (M+H)$^+$, 454.5697 (M+Na)$^+$, 470.7429 (M+K)$^+$; HRMS:m/z calcd for C$_{27}$H$_{30}$NO$_4$ 432.2166, found 432.2169.

Example 1 (F)

Preparation of (5S,6R)-4,5-Bis(benzyloxy)-6-(benzyloxymethyl)piperidin-2-one (5b)

Compound 3b (437 mg, 1 mmol) was dissolved in a mixture of MeCN (15 mL) and HCOOH (3.0 mL). To this mixture, NaCNBH$_3$ (133 mg, 2 eqs.) was added and the reaction mixture was refluxed at 85° C. for 4.5 h. The reaction mixture was then cooled in an ice-bath and the reaction was quenched by adding aq. HCl solution (0.1 N, 30 mL). After stirring for another 15 minutes, EtOAc (50 mL) and then saturated aq. NaHCO$_3$ solutions (50 mL) were added to it. The water layer was separated and extracted with EtOAc (2×25 mL), the combined organic fractions were pooled and then washed with brine (1×30 mL) and dried (anhyd. Na$_2$SO$_4$). After concentration in vacuo, the resulting crude was purified by SiO$_2$ column chromatography (EtOAc-petroleum ether, 4:6) to afford a colorless semi-solid 5b (250 mg 59%).

R$_f$ 0.21 (EtOAc-petroleum ether); [α]$^{20}$$_D$+29.43 (c1.1, CHCl$_3$); IR (CHCl$_3$): ν$_{max}$ 3395, 3017, 2926, 1663, 1454, 1216, 1114, 756, 698, 668 cm$^{-1}$; $^1$H NMR (200 MHz, CDCl$_3$): δ$_H$ 7.40-7.25 (m, 15H, ArH), 6.06 (bs, 1H, NH) 4.97-4.39 (m, 6H, PhCH$_2$), 4.00 (bs, 1H, H-4), 3.89-3.79 (ddd, 1H, J=10.6, 6.3, 1.6 Hz, H-5), 3.59-3.48 (m, 3H, H-6, H-3), 2.91-2.63 (m, 2H, H-2); $^{13}$C NMR (50 MHz, CDCl$_3$): δ$_C$ 170.2 (q, C-1), 138.1, 137.7, 137.4 (q, Ar), 128.6, 128.6, 128.4, 128.0, 128.0, 127.9, 127.8, 127.5 (d, Ar), 75.6 (s, C-4), 73.9, 73.6, 71.7 (s, C-3), 70.9, 70.6 (d, PhCH$_2$, C-6), 54.9 (s, C-5), 33.7 (d, C-2); ESI-MS: m/z 432.3909 (M+H)$^+$, 454.3993 (M+Na)$^+$, 470.3436 (M+K)$^+$; HRMS: m/z calcd for C$_{27}$H$_{29}$NO$_4$ 432.2169, found 432.2170.

Example 1 (G)

Preparation of (2R,3R,4R)-3,4-Bis(benzyloxy)-2-(benzyloxymethyl)piperidine (6a)

To a solution of 5a (256 mg, 0.594 mmol) in THF (15 mL), LAH (68 mg, 3 eqs.) was added. The reaction mixture was stirred for 4 h at 70° C. under nitrogen atmosphere. The mixture was then brought to room temperature 30° C. and poured into a mixture of diethyl ether and ice water (1:1, 100 mL). After stirring for 15 minutes, 0.5 M aq. NaOH (75 mL) was added and the mixture was stirred for another 10 minutes. The water layer was then separated and extracted with diethyl ether (3×50 mL), the organic fractions were pooled, washed with brine and finally dried (anhyd. Na$_2$SO$_4$) and concentrated in vacuo. The crude product was purified by SiO$_2$ column chromatography (EtOAc-petroleum ether, 1:1) to afford 6a (120 mg, 49%) as a yellow syrup;

R$_f$ 0.12 (EtOAc-petroleum ether, 1:1); [α]$^{20}$$_D$+21.76 (c 1.1, CHCl$_3$); IR (CHCl$_3$): ν$_{max}$ 3151, 3017, 2922, 1398, 1220, 1099, 772, 669, 615 cm$^{-1}$; $^1$H NMR (200 MHz, CDCl$_3$): δ$_H$ 7.38-7.21 (m, 15H, ArH), 4.98-4.47 (m, 6H, PhCH$_2$), 3.76-3.73 (dd, 1H, J=2.5, 9.0 Hz, H-6$_a$), 3.62-3.52 (m, 2H, H-6$_b$, H-3), 3.39-3.34 (t, H-1, J=9.0 Hz, H-4), 3.10-3.05 (ddd, 1H, J=1.8, 2.3, 12.6 Hz, H-1$_a$), 2.76-2.71 (m, 1H, H-5), 2.62-2.56 (dt, 1H, J=12.6, 2.3 Hz, H-1$_b$), 2.34 (bs, 1H, NH), 2.20-2.14 (m, 1H, H-2$_a$), 1.57-1.50 (m, 1H, H-2$_b$); $^{13}$C NMR (50 MHz, CDCl$_3$): δ$_C$ 138.8, 138.7, 138.2 (q, Ar), 128.4, 128.4, 128.4, 128.1, 127.9, 127.7, 127.7, 127.6, 127.6 (s, Ar), 82.5 (s, C-3), 80.8 (s, C-4), 75.2, 73.4, 71.5 (d, PhCH$_2$), 70.7 (d, C-6), 60.1 (s, C-5), 43.6 (d, C-1), 32.1 (d, C-2); ESI-MS: m/z 418.4191 (M+H)$^+$; HRMS: m/z calcd for C$_{27}$H$_{31}$NO$_3$ 418.2377, found 418.2378.

Example 1 (H)

Preparation of (2R,3S,4R)-3,4-Bis(benzyloxy)-2-(benzyloxymethyl)piperidine (6b)

To a solution of 5b (242 mg, 0.58 mmol) in THF (15 mL), LAH (65 mg, 3 eqs.) was added. The reaction mixture was stirred for 2 h at 70° C. under nitrogen atmosphere. The reaction mixture was then brought to room temperature 25° C. and poured into a mixture of diethyl ether and ice water (1:1, 100 mL). After stirring for 15 minutes, aq. NaOH (0.5 M, 75 mL) was added and the reaction mixture was stirred for another 10 minutes. The water layer was then separated and extracted with diethyl ether (3×50 mL), the organic fractions were pooled and washed with brine (1×30 mL) and dried (anhyd. Na$_2$SO$_4$). After concentration in vacuo, the reaction mixture was purified by SiO$_2$ column chromatography (EtOAc-petroleum ether, 1:1) to afford 6b (95 mg, 41%) as a yellow syrup;

R$_f$ 0.12 (EtOAc-petroleum ether); [α]$^{20}$$_D$ −4.07 (c 1.0, CHCl$_3$); IR (CHCl$_3$): ν$_{max}$ 3302, 3089, 3066, 3019, 2929, 1455, 1365, 1216, 1088, 751, 699, 669 cm$^{-1}$; $^1$H NMR (400 MHz, CDCl$_3$): δ$_H$ 7.40-7.28 (m, 15H, ArH), 5.01-4.46 (m, 6H, PhCH$_2$), 3.98 (bs, 1H, H-4), 3.59-3.55 (m, 1H, H-6$_a$), 3.53-3.49 (m, 1H, H-3), 3.48-3.44 (t, H-1, J=8.5, 7.8 Hz, H-6$_b$), 3.32 (1H, bs, NH), 3.17-3.13 (dd, 1H, J=13.3, 2.0 Hz, H-1$_a$), 2.85-2.81 (t, 1H, J=6.8 Hz, H-5), 2.66-2.58 (dt, 1H, J=12.8, 3.0, 3.0, 2.8 Hz, H-1$_b$), 2.05-1.94 (m, 1H, H-2$_a$), 1.86-1.83 (dd, 1H, J=12.4, 2.2 Hz, H-2$_b$); $^{13}$C NMR (100 MHz, CDCl$_3$): δ$_C$ 139.1, 138.7, 138.1 (q, Ar), 128.5, 128.2, 128.0, 127.6, 127.3 (s, Ar), 79.7 (s, C-3), 74.1, 73.5, 70.1 (d, PhCH$_2$), 73.3 (s, C-4), 70.4 (d, C-6), 58.8 (s, C-5), 44.2 (d, C-1), 27.7 (d, C-2); ESI-MS: m/z 418.0585 (M+H)$^+$; HRMS: m/z calcd for C$_{27}$H$_{32}$NO$_3$ 418.2377, found 418.2377.

Example 1 (I)

Preparation of (+)-Fagomine (7a)

To a solution of 6a (100 mg, 0.24 mmol) in AcOH (2.5 ml) was added 10% palladium on active charcoal (10 mg) at room temperature 27° C. and the mixture stirred overnight for 12 h under hydrogen gas. The reaction mixture was filtered through a celite pad and washed with MeOH (50 mL), the filtrate was concentrated in vacuo. The residue was dissolved in water (5 mL) and the solution was stirred at room temperature 25° C. with Amberlite IR-120 (H$^+$) for 3 h. The suspension was eluted with water and then 0.5 M NH$_4$Cl to furnish pure (+)-fagomine (7a) (31 mg, 87%), which was identified on the basis of comparison with reported spectral data.

Example 1 (J)

Preparation of 4-epi-Fagomine (7b)

Similarly, 7b (30 mg, 86%) was obtained from 6b (100 mg, 0.24 mmol) by following the above-mentioned procedure.

Example 2

Preparation of 3-deoxynojirimycin (10)

Example 2 (A)

Preparation of Tert-butyl (2R,3R,4S)-3,4-bis(benzyloxy)-2-((benzyloxy)methyl)-6-oxopiperidine-1-carboxylate (8a)

Glycolactam 5a (150 mg, 0.35 mmol) was dissolved in DCM (10 mL), Et$_3$N (48.8 μL, 0.35 mmol) was added and cooled to 0° C., Boc$_2$O (152 mg, 0.70 mmol) was then added followed by DMAP (43 mg, 0.35 mmol) and stirred at 25° C. for 9 h. The reaction mixture was evaporated to dryness and subjected to SiO$_2$ column chromatography (EtOAC-Et$_3$N-petroleum ether, 5:2:93) to afford 8a (175 mg, 82%) as an oily syrup;

R$_f$ 0.76 (EtOAc-petroleum ether, 1:1); [α]$^{25}_D$-49.53 (c 1.12, CHCl$_3$); IR (CHCl$_3$): ν$_{max}$ 3021, 2978, 2402, 2360, 1767, 1718, 1511, 1220, 1034, 789, 734, 670 cm$^{-1}$; $^1$H NMR (200 MHz, CDCl$_3$): δ$_H$ 7.33-7.25 (m, 15H, ArH), 4.76-4.45 (m, 7H), 4.05-4.01 (dd, 1H, J=5.9, 2.4 Hz, 1H), 3.91-3.81 (m, 1H), 3.71-3.63 (m, 1H), 3.55-3.48 (m, 1H), 2.92-2.81 (dd, 1H, =16.8, 5.1 Hz), 2.70-2.57 (dd, 1H, J=16.8, 8.7 Hz), 1.48 (s, 9H); $^{13}$C NMR (50 MHz, CDCl$_3$): δ$_C$ 169.6, 152.2, 137.8, 128.5, 128.0, 127.9, 127.8, 127.6, 83.4, 75.5, 73.2, 72.3, 71.6, 70.4, 59.0, 37.6, 28.0; ESI-MS: m/z 554.23 (M+Na)$^+$; HRMS: m/z calcd for C$_{32}$H$_{37}$NO$_6$Na 554.2513 (M+Na)$^+$, found 554.2513.

Example 2 (13)

Preparation of Tert-butyl (2R,3S,4S)-3,4-Bis(benzyloxy)-2-((benzyloxy)methyl)-6-oxopiperidine-1-carboxylate (8b)

Similarly 8b was obtained from 5b by following abovementioned procedure. The crude reaction mixture was purified by SiO$_2$ column chromatography (EtOAC-Et$_3$N-petroleum ether, 5:2:93) to afford 8b as an oily syrup (143 mg, 79%);

R$_f$ 0.57 (EtOAc-petroleum ether, 1:1); [α]$^{25}_D$+1.16 (c 1.14, CHCl$_3$); IR (CHCl$_3$): ν$_{max}$ 3014, 2362, 1741, 1707, 1657, 1516, 1265, 1033, 812, 759, 674 cm$^{-1}$; $^1$H NMR (200 MHz, CDCl$_3$): δ$_H$ 7.34-7.24 (m, 15H), 4.86-4.46 (m, 6H), 4.40-4.30 (m, 1H), 4.16-4.13 (m, 1H), 3.92-3.85 (m, 2H), 3.77-3.69 (m, 1H), 3.02-2.89 (dd, 1H, J=17.2, 9.2 Hz), 2.77-2.66 (dd, 1H, J=17.2, 5.7 Hz), 1.45 (s, 9H); $^{13}$C NMR (50 MHz, CDCl$_3$): δ$_C$ 168.6, 152.5, 138.1, 138.0, 137.8, 128.5, 128.4, 128.0, 127.7, 127.5, 83.7, 73.7, 73.5, 73.3, 73.1, 71.4, 68.9, 57.1, 37.0, 27.8; ESI-MS: m/z 554.27 (M+Na)$^+$; HRMS: m/z calcd for C$_{32}$H$_{37}$NO$_6$Na 554.2513 (M+Na)$^+$, found 554.2521.

Example 2 (C)

Preparation of Tert-butyl (2R,3R)-3,4-bis(benzyloxy)-2-((benzyloxy)methyl)-6-hydroxypiperidine-1-carboxylate (9a)

N-Boc protected lactam 8a (100 mg, 0.188 mmol) was dissolved in dry toluene (5.0 mL) and cooled to –76° C. under inert atmosphere, and superhydride (1.0 M in THF) (0.21 mL, 1.12 eq) was added slowly drop wise over a period of 10 min, and stirred at –76° C. for 1 h. Saturated NH$_4$Cl soln (4.0 mL) was added and stirred further for 1.5 h at –76° C., and then temp was raised to room temperature 35° C. and stirred at room temperature 35° C. for 10 h. Reaction mixture was then treated with 10% Na$_2$CO$_3$ soln (4.0 mL) and DCM (10 mL) was added to the reaction mixture. The organic layer was separated, and the aq. layer was extracted with DCM (3×5 mL). All the organic layers were pooled together, dried (anhyd. Na$_2$SO$_4$), concentrated in vacuo and finally purified by SiO$_2$ column chromatography (EtOAC-Et$_3$N-petroleum ether, 5:1:44) to afford 9a as a viscous oil (94 mg, 94%);

R$_f$ 0.38 (EtOAc-petroleum ether, 3:7); [α]$^{25}_D$-47.44 (c1.21, CHCl$_3$); IR (CHCl$_3$): ν$_{max}$ 3741, 3019, 2362, 2334, 1692, 1531, 1216, 757, 695, 672 cm$^{-1}$; $^1$H NMR (200 MHz, CDCl$_3$): δ$_H$ 7.30-7.25 (m, 15H), 5.64 (brs, 1H), 4.71-4.48 (m, 6H), 4.05-4.01 (m, 2H), 3.85-3.68 (m, 2H), 3.62-3.50 (m, 2H), 2.26-2.15 (m, 1H), 2.04-1.90 (m, 1H), 1.69 (brs, 1H), 1.46 (s, 9H); $^{13}$C NMR (50 MHz, CDCl$_3$): δ$_C$ 156.7, 138.2, 138.1, 137.5, 128.5, 128.4, 128.0, 127.7, 127.7, 127.5, 80.8, 77.3, 74.8, 73.2, 72.9, 71.7, 71.5, 30.9, 28.4; ESI-MS: m/z 556.27 (M+Na)$^+$; HRMS: m/z calcd for C$_{32}$H$_{39}$NO$_6$Na 556.2670, found 556.2670.

Example 2 (D)

Preparation of 3-DeoxyNojirimycin (10)

A mixture of 9a (100 mg, 0.19 mmol) and 10% aq. HCL (5 mL) in MeOH (5.0 ml) was stirred at 70° C. for 5 h. The reaction mixture was basified with 2M NaOH at 0° C. The resulting mixture was extracted with DCM (3×10 mL). The combined organic layers were pooled and dried (anhyd. Na$_2$SO$_4$) and concentrated in vacuo. The residue was dissolved in AcOH (2.5 ml) and 10% palladium on active charcoal (10 mg) was added at room temperature 25° C. and the mixture stirred overnight for 12 h under hydrogen gas. The reaction mixture was filtered through a celite pad and washed with MeOH (50 mL), the filtrate was concentrated in vacuo. The residue was dissolved in water (5 mL) and the solution was stirred at room temperature 25° C. with Amberlite IR-120 (H$^+$) for 3 h. The suspension was eluted with water and then 0.5 M NH$_4$Cl to furnish pure 3-deoxyNojirimycin (10) (17 mg, 56%).

Example 3 (A)

Preparation of Tert-butyl (2R,3R)-3,4-bis(benzyloxy)-2-((benzyloxy)methyl)-3,4-dihydropyridine-1 (2H)-carboxylate (11a)

N-Boc protected lactam 8a (136 mg, 0.26 mmol) was dissolved in dry toluene (3 mL) and cooled to –70° C. under inert atmosphere, and superhydride (1.0 M in THF) was added slowly drop wise over a period of 10 min, and stirred at –70° C. for 30 min. TFAA (0.31 mL, 2.2 mmol) was added followed by addition of DIPEA (1.5 mmol) and catalytic amount of DMAP. Temperature is then raised from −70° C. to room temperature 30° C. in 8 h and stirred further for 3 h at 25° C. Water was added (10 mL), organic layer was separated, washed with water (2×10 mL), dried (anhyd. $Na_2SO_4$), concentrated in vacuo and purified by $SiO_2$ column chromatography (EtOAC-$Et_3$N-petroleum ether, 3:2: 95) to afford 11a as a viscous oil (119 mg, 90%);

$R_f$ 0.57 (EtOAc-petroleum ether, 1:1); $[\alpha]^{25}_D$-97.97 (c1.10, $CHCl_3$); IR ($CHCl_3$): $\nu_{max}$ 3739, 3426, 2362, 2334, 1645, 1547, 1365, 924, 800, 699 $cm^{-1}$; $^1$H NMR (500 MHz, $CDCl_3$): $\delta_H$ 7.35-7.24 (m, 15H), 7.11-6.93 (m, 1H), 5.10-4.90 (m, 1H), 4.74-4.56 (m, 3H), 4.52-4.39 (m, 4H), 4.19-4.13 (m, 1H), 3.86-3.57 (m, 3H), 1.54-1.49 (m, 9H); $^{13}$C NMR (125 MHz, $CDCl_3$, mixture of isomers): $\delta_C$ 152.3, 138.8, 138.6, 138.3, 138.0, 128.6, 128.5, 128.4, 128.2, 127.7, 127.4, 127.3, 126.9, 126.6, 101.5, 81.5, 81.4, 77.9, 77.8, 75.6, 75.1, 73.1, 72.9, 72.9, 72.8, 72.7, 71.9, 71.5, 71.2, 71.1, 70.9, 70.7, 70.4, 70.2, 68.4, 66.9, 66.8, 66.5, 66.0, 53.3, 52.7, 50.8, 28.2, 28.1, 27.9; ESI-MS: m/z 538.27 (M+Na)$^+$; HRMS: m/z calcd for $C_{32}H_{37}NO_5Na$ 538.2564, found 538.2564.

Example 3 (B)

Preparation of Tert-butyl (2R,3S)-3,4-bis(benzyloxy)-2-((benzyloxy)methyl)-3,4-dihydropyridine-1 (2H)-carboxylate (11b)

Similarly 11b was obtained from 8b (283 mg, 0.533 mmol) by following the same procedure described above as a pale yellow viscous oil (238 mg, 87%) after purification by $SiO_2$ column chromatography (EtOAC-$Et_3$N-petroleum ether, 3:2:95);

$R_f$ 0.57 (EtOAc-petroleum ether, 1:1); $[\alpha]^{25}_D$-56.21 (c 1.13, $CHCl_3$); IR ($CHCl_3$): $\nu_{max}$ 3740, 3620, 2362, 2334, 1647, 1547, 1367, 921, 821, 678 $cm^{-1}$; $^1$H NMR (200 MHz, $CDCl_3$): $\delta_H$ 8.29 (m, 1H), 7.35-7.22 (m, 15H), 4.89-4.77 (m, 2H), 4.70-4.61 (m, 3H), 4.52-4.29 (m, 2H), 3.99-3.95 (m, 2H), 3.85-3.73 (m, 1H), 3.64-3.44 (m, 1H), 1.48-1.46 (m, 9H); $^{13}$C NMR (50 MHz, $CDCl_3$): $\delta_C$ 150.9, 138.8, 138.3, 137.5, 128.6, 128.5, 128.2, 128.1, 128.1, 127.7, 127.7, 127.6, 127.5, 127.4, 110.5, 75.6, 75.1, 72.9, 71.6, 68.5, 67.7, 63.8, 62.8, 58.0, 27.7; ESI-MS: m/z 538.08 (M+Na)$^+$; HRMS: m/z calcd for $C_{32}H_{37}NO_5Na$ 538.2564, found 538.2565.

Example 4 tert-Butyl (2R,3R,5S,6S)-3,4-bis(benzyloxy)-2-((benzyloxy)methyl)-5,6-dihydroxypiperidine-1-carboxylate (12a)

(DHQD)$_2$AQN (4.16 mg, 0.00485 mmol, 5 mol %), $K_3Fe(CN)_6$ (96 mg, 0.291 mmol, 3 eq), $K_2CO_3$ (93.7 mg, 0.679 mmol, 70 eq), and $K_2OsO_2(OH)_4$ (2 mg, 0.00543 mmol. 5.59 mol %) were dissolved in tert-butyl alcohol and water (5 ml each) at room temperature 25° C. $CH_3SO_2NH_2$ (18.43 mg, 0.194 mmol, 2.0 eq) was added. The solution was cooled to 0° C. and Boc-iminoglycal 11a was added (50 mg, 0.097 mmol). The mixture was stirred at 0° C. for 60 h. In the work up $Na_2SO_3$ (200 mg) was slowly added and the suspension was warmed to room temperature 25° C. with vigorous stirring. Ethyl acetate was added and the aq. layer was further extracted with EtOAc (2×5 ml), the combined organic layers were washed with 2M NaOH (20 ml). The combined org layers were dried over $Na_2SO_4$ and concentrated in vacuo, which on preparative TLC separation (20% EtOAc-Pet ether) furnished 12a (38 mg, 30%), $R_f$ 0.23 (EtOAc-petroleum ether, 7:3); $[\alpha]^{25}_D$-18.79 (c 1.15%, $CHCl_3$); $\nu_{max}$ ($CHCl_3$)/$cm^{-1}$, 667; $\delta_H$ (200 MHz, $CDCl_3$) 7.39-7.24 (m, 15H), 5.69-5.56 (m, 1H), 4.69-4.48 (m, 6H), 4.19-4.08 (m, 1H), 3.99-3.93 (m, 1H), 3.87-3.85 (m, 2H), 3.78-3.69 (m, 1H), 3.63-3.55 (m, 1H), 2.74 (brs, 1H), 1.79 (brs, 1H), 1.53-1.47 (m, 9H); $\delta_C$ (50 MHz, $CDCl_3$) 155.4, 138.2, 138.0, 137.7, 128.7, 128.6, 128.5, 128.4, 128.4, 128.3, 128.2, 128.1, 128.0, 128.0, 127.9, 127.7, 127.6, 81.7, 78.3, 77.2, 77.0, 73.1, 71.5, 70.0, 65.6, 28.3; ESI-MS: m/z 572.27 (M+Na)$^+$; HRMS: m/z calcd for $C_{32}H_{39}NO_7Na^+$ 572.2619, found 572.2621.

Example 5

Tert-Butyl (2R,3R,5R,6R)-3,4-bis(benzyloxy)-2-((benzyloxy)methyl)-5,6-dihydroxypiperidine-1-carboxylate (13a)

(DHQ)$_2$AQN (5.0 mg, 0.0058 mmol, 5 mol %), $K_3Fe(CN)_6$ (118 mg, 0.358 mmol, 3 eq), $K_2CO_3$ (114 mg, 0.826 mmol, 70 eq), and $K_2OsO_2(OH)_4$ (2.5 mg, 0.0068 mmol, 5.59 mol %) were dissolved in tert-butyl alcohol and water (6 ml each) at room temperature 30° C. $CH_3SO_2NH_2$ (23 mg, 0.242 mmol, 2.0 eq) was added. The solution was cooled to 0° C. and Boc-iminoglycal 11a was added (61 mg, 0.118 mmol). The mixture was stirred at 0° C. for 66 h. In the work up, $Na_2SO_3$ (200 mg) was slowly added and the suspension was warmed to room temperature 30° C. with vigorous stirring. EtOAc was added and the aq layer was further extracted with ethyl acetate (2×5 ml), the combined organic layers were washed with 2M NaOH (20 ml). The combined org layers were dried over $Na_2SO_4$ and concentrated in vacuo, which on preparative TLC separation (EtOAc-petroleum ether, 7:3) furnished 13a (20 mg, 71%), $R_f$ 0.21 (EtOAc-petroleum ether, 7:3); $[\alpha]^{25}_D$-13.33 (c 1.1%, $CHCl_3$); $\nu_{max}$ ($CHCl_3$)/$cm^{-1}$ 3443, 3064, 2927, 2859, 2362, 2334, 1690, 1499, 1368, 1086, 757, 699, 669; $\delta_H$ (200 MHz, $CDCl_3$) 7.35-7.26 (m, 15H), 5.65-5.52 (m, 1H), 4.70-4.41 (m, 6H), 4.24-4.04 (m, 1H), 3.95-3.89 (m, 1H), 3.85-3.80 (m, 1H), 3.75-3.63 (m, 2H), 3.58-3.45 (m, 1H), 2.68 (brs, 1H), 1.68 (brs, 1H), 1.48-1.40 (m, 9H); $\delta_c$ (50 MHz, $CDCl_3$) 154.1, 138.1, 137.5, 137.4, 128.7, 128.6, 128.5, 128.5, 128.3, 128.3, 128.2, 128.1, 128.0, 127.9, 127.8, 127.6, 81.7, 81.4, 78.6, 77.3, 75.3, 73.4, 72.5, 64.2, 61.4, 28.4; ESI-MS: m/z 572.26 (M+Na)$^+$; HRMS: m/z calcd for $C_{32}H_{39}NO_7Na^+$ 572.2619, found 572.2619.

ADVANTAGES OF INVENTION

- Novel route of synthesis of alkaloids
- Provides reasonable good yields
- Piperidine alkaloids are not known to be synthesized from gluconolactone
- Other methods of synthesis are known, but this process is shorter, enantiomeric tuning is possible depending on starting enantiomer used.

We claim:
1. A process for the preparation of piperidine alkaloids, the process comprising:
   a) dissolving gluconolactone compound (1) in methanolic ammonia solution followed by stirring at room temperature in the range of 20 to 35° C. for 1 to 1.5 h to afford 5-δ-hydroxy amide (2);

1a R₁ = R₂ = H, R₃ = OBn, R₄ = H
1b R₁ = R₂ = H, R₃ = H, R₄ = OBn

2a R₁ = R₂ = H, R₃ = OBn, R₄ = H
2b R₁ = R₂ = H, R₃ = H, R₄ = OBn b) stirring a solution of compound 2 as obtained in step (a) in DMSO and Ac₂O at room temperature in the range of 20 to 35° C. for period in the range of 22 to 23 h followed by addition of water to afford δ-keto amide (3);

3a R₁ = R₂ = H, R₃ = OBn, R₄ = H
3b R₁ = R₂ = H, R₃ = H, R₄ = OBn c) adding formic acid and sodium cyanoborohydride to a solution of compound 3 as obtained in step (b) in acetonitrile followed by refluxing at temperature in the range of 80 to 85° C. for period in the range of 4 to 4.5 h to afford glycolactam compound (5);

5a R₁ = R₂ = H, R₃ = OBn, R₄ = H
5b R₁ = R₂ = H, R₃ = H, R₄ = OBn d) adding lithium aluminium hydride to a solution of compound 5 as obtained in step (c) in tetrahydrofuran followed by stirring the reaction mixture for period in the range of 3.5 to 4 h at temperature in the range of 65 to 70° C. and purification to afford protected piperidine compound (6);

6a R₁ = R₂ = H, R₃ = OBn, R₄ = H
6b R₁ = R₂ = H, R₃ = H, R₄ = OBn e) adding palladium on active charcoal to a solution of piperidine compound 6 as obtained in step (d) in acetic acid followed by stirring the mixture for overnight for period in the range of 10 to 12 hr at room temperature in the range of 20 to 35° C. under hydrogen atmosphere to afford piperidine alkaloids (7);

7a R₁ = R₂ = H, R₃ = OH, R₄ = H, (+)-Fagomine
7b R₁ = R₂ = R₃ = H, R₄ = OH, 4-epi-Fagomine f) adding Et₃N to a solution of glycolactam (5) as obtained in step (c) in dichloromethane followed by cooling to 0° C. and further adding Boc₂O, DMAP followed by stirring at temperature in the range of 20 to 25° C. for period in the range of 8 to 9 h to afford N-Boc protected lactam (8);

8a R₁ = R₂ = H, R₃ = OBn, R₄ = H
8b R₁ = R₂ = H, R₃ = H, R₄ = OBn g) dissolving N-Boc protected lactam (8a) of step (d) in toluene and cooling to −76° C. under inert atmosphere and adding superhydride and ammonium chloride solution at −76° C. followed by stirring the reaction mixture for period in the range of 9 to 10 h at room temperature to afford lactamol compound 9a;

9a R$_1$ = R$_2$ = H, R$_3$ = OBn, R$_4$ = H h) stirring a mixture of compound of step (e) and HCl in methanol at 70° C. for 5 h followed by basifying the reaction mixture to afford 3-deoxynojirimycin (10a);

10a R$_1$ = R$_2$ = H, R$_3$ = OH, R$_4$ = H i) dissolving N-Boc protected lactam (8a) of step (d) in dry toluene and cooled at −76° C. under inert atmosphere and adding superhydride with stirring followed by addition of TFAA, DIPEA, catalytic amount of DMAP and purification to afford Boc-iminoglycal (11a/11b); and j) adding Boc-iminoglycal (11a) to a solution of (DHQ)$_2$AQN, K$_3$Fe(CN)$_6$, K$_2$CO$_3$, K$_2$OsO$_2$(OH)$_4$ and CH$_3$SO$_2$NH$_2$ in tert-butyl alcohol and water cooled at 0° C. followed by stirring the mixture at 0° C. for 60 to 66 h to afford iminoglycal compound (12a).

2. The process as claimed in claim 1, wherein the piperidine alkaloids are (+)-fagomine (7a), 4-epi-fagomine (7b), 3-deoxynojirimycin (10a), Boc-iminoglycal (11a/11b), iminoglycal compound (12a) and iminoglycal compound (13a).

3. The process as claimed in claim 1, wherein the steps (a), (b) and (d) are carried out under nitrogen atmosphere.

4. The process as claimed in claim 1, wherein the Boc-iminoglycal is tert-butyl (2R,3R)-3,4-bis(benzyloxy)-2-((benzyloxy)methyl)-3,4-dihydropyridine-1(2H)-carboxylate (11a), tert-butyl (2R,3S)-3,4-bis(benzyloxy)-2-((benzyloxy)methyl)-3,4-dihydropyridine-1(2H)-carboxylate (11b).

5. The process as claimed in claim 1, wherein the iminoglycal compound is tert-Butyl (2R,3R,5R,6R)-3,4-bis(benzyloxy)-2-((benzyloxy)methyl)-5,6-dihydroxy-piperidine-1-carboxylate (12a) or tert-Butyl (2R,3R,5S,6S)-3,4-bis(benzyloxy)-2-((benzyloxy)methyl)-5,6-dihydroxypiperidine-1-carboxylate (13a).

6. The process as claimed in claim 1, wherein said process may also comprise adding Boc-iminoglycal (11a) to a solution of (DHQD)$_2$AQN, K$_3$Fe(CN)$_6$, K$_2$CO$_3$, K$_2$OsO$_2$(OH)$_4$ and CH$_3$SO$_2$NH$_2$ in tert-butyl alcohol and water cooled at 0° C. followed by stirring the mixture at 0° C. for 60 to 66 h to afford iminoglycal compound (13a).

* * * * *